US006946000B2

United States Patent
Senegas et al.

(10) Patent No.: US 6,946,000 B2
(45) Date of Patent: Sep. 20, 2005

(54) INTERVERTEBRAL IMPLANT WITH DEFORMABLE WEDGE

(75) Inventors: Jacques Senegas, Merignac (FR); Denis Pasquet, Pessac (FR); Régis Le Couedic, Bordeaux (FR)

(73) Assignee: Spine Next, Bordeaux (FR)

( * ) Notice: Subject to any disclaimer, the term of this patent is extended or adjusted under 35 U.S.C. 154(b) by 54 days.

(21) Appl. No.: 10/332,798

(22) PCT Filed: Dec. 20, 2001

(86) PCT No.: PCT/FR01/04094

§ 371 (c)(1),
(2), (4) Date: Jan. 9, 2003

(87) PCT Pub. No.: WO02/051326

PCT Pub. Date: Jul. 4, 2002

(65) Prior Publication Data

US 2004/0024458 A1 Feb. 5, 2004

(30) Foreign Application Priority Data

Dec. 22, 2000 (FR) .......................................... 00 16857

(51) Int. Cl.[7] ................................................. A61F 2/44
(52) U.S. Cl. ...................................... 623/17.11; 606/61
(58) Field of Search .......................... 623/17.11; 606/61

(56) References Cited

U.S. PATENT DOCUMENTS

| 5,496,318 A | * | 3/1996 | Howland et al. | ............. 606/61 |
| 5,836,948 A | * | 11/1998 | Zucherman et al. | .......... 606/61 |
| 6,602,293 B1 | * | 8/2003 | Biermann et al. | ......... 623/23.5 |

FOREIGN PATENT DOCUMENTS

| FR | 2 722 088 | 1/1996 |
| FR | 2 775 183 | 8/1999 |
| WO | WO 97/09000 | 3/1997 |
| WO | WO 99/40866 | 8/1999 |

* cited by examiner

Primary Examiner—Thomas Barrett
(74) Attorney, Agent, or Firm—Merchant & Gould P.C.

(57) ABSTRACT

The invention relates to an intervertebral implant including a wedge which is inserted between two spinous processes and has two opposite grooves in which said spinous processes engage, which grooves have substantially parallel axes, and each of which grooves is defined by two flanges. The wedge has at least one central opening between said two grooves and said central opening passes completely through said wedge along an axis Ac substantially parallel to the axes Ag1 and Ag2 of said grooves, which renders said wedge elastically deformable.

16 Claims, 2 Drawing Sheets

INTERVERTEBRAL IMPLANT WITH DEFORMABLE WEDGE

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

FIELD OF THE INVENTION

The present invention relates to an intervertebral implant including a wedge adapted to be inserted between two spinous processes, said wedge having two opposite grooves each defined by two flanges, the sea of acid two grooves being substantially parallel to each other and said spinous processes engaging in said two groove. The present invention also relates to a method of manufacturing as intervertebral implant, in particular the above defined type.

BACKGROUND OF THE INVENTION

Intervertebral implants including a wedge which is inserted between the spinous processes which extend the posterior part of two consecutive vertebrae and which limits movement towards each other of the two vertebrae are well known in the art.

Degenerative pathologies of the intervertebral disc cause the vertebrae to move towards each other, possibly in the extent of coming into contact, which can pinch the roots of nerves routed laterally between the vertebrae. To remedy this, a wedge is fixed between the spinous processes of the two consecutive vertebrae that can come into contact on movement of the spine, using appropriate fixing means. The wedge therefore blocks the movement of the vertebrae towards each other, in particular when the spine it extended.

The wedges are made from a rigid biocompatible alloy, usually one based on titanium, and cannot be deformed by the forces that are applied to them, unlike the normal intervertebral disc, which is elastically deformable within certain limits. Thus although the wedges prevent contact between two vertebrae, they constitute an incomplete replacement for the intervertebral disc, which allows relative movement of the vertebrae.

To obtain wedges that are elastically deformable, wedges have been envisaged having two opposite rigid material members forming grooves in which the spinous processes of the two vertebrae engage, the two members forming the grooves being connected together by two elastically deformable leaf spring portions. Thus the wedge as a whole is elastically deformable, which gives it properties adapted to reproduce the normal physiological conditions of relative movement of the vertebrae.

However, the above type of wedge is relatively complicated to manufacture and the materials of the leaf springs are usually not biocompatible. What is more, the springs must be relatively large to achieve the necessary elasticity, and then take up a great deal of room.

Accordingly, wedges have been envisaged that are easier to produce, being made in one piece from a rigid material obtained by polymerization and having a modulus of elasticity much lower than the modulus of elasticity of titanium. However, the modulus of elasticity of the material must be sufficient for the grooves of said wedges to be able to immobilize the spinous processes correctly, and for the reason, although they are more deformable than titanium alloy wedges, they are not sufficiently deformable to fulfill their function.

OBJECTS AND SUMMARY OF THE INVENTION

According to a first aspect, the invention aims to propose an intervertebral implant including a deformable wedge made from a rigid material obtained by polymerization.

According to do invention, the above object is achieved by virtue of the fact that the wedge has a central opening between said two grooves, said central opening passes completely through said wedge along an axis substantially parallel to said axes of said grooves, and the volume of said central opening is from 10% to 30% of the total volume of said wedge, which renders said wedge elastically deformable.

Thus one feature of the invention is the provision of a central opening in a relatively undeformable solid wedge to obtain walls mobile relative to each other so that the wedge can deform elastically without being made excessively fragile. Because of the void between said walls, the walls can deform elastically under load at the base of each groove, in particular when the spinous processes move towards each other.

The wedge therefore constitutes an obstacle to movement the vertebrae towards each other. However, the forces exerted by the wedge on the spinous processes are proportional to the relative movements of the two vertebrae, since the wedge is elastically deformable, which reproduces normal or virtually normal physiological conditions of relative movement of the vertebrae.

In a first particular embodiment of the invention the opening has a substantially rectangular parallelepiped shape with two parallel faces perpendicular to an axis intersecting the axes of said grooves at right angles.

Thus the bottom of the two grooves is constituted by a wall and the walls of the two grooves are substantially parallel to each other and perpendicular to the main direction of movement towards each other of the two vertebrae. The wedge therefore has a large amplitude of deformation, in particular in compression.

In a second particular embodiment the invention the wedge has two superposed openings between said two grooves and the axes of said openings and the axes of said two grooves are substantially parallel to each other.

In this particular embodiment, the two openings produce three partitions adapted to be deformed elastically by a load normal to said partitions.

In a preferred embodiment of the invention the implant further includes a fixing band adapted to retain said wedge between said processes and said wedge has fixing means for connecting said band to said wedge and self-locking fixing means in its lateral walls adopted to receive said fixing band in order to immobilize it relative to said wedge.

The fixing band is therefore pre-mounted on the wedge, before the surgical procedure, and the surgeon can insert the wedge between the spinous processes and then fasten it to the processes by pulling on the free end of the band, which wedges in the self-locking fixing means.

The fixing means are advantageously formed in said wedge by at least one lateral bore in one of said flanges opening into one of said grooves. Accordingly, the end of the band opposite said free end is connected to said wedge, forming a loop passing through the lateral bore. The band is clipped to itself. Of course, the lateral bore is only for fixing the end of the band, and is separate from said central opening, which is exclusively for making the wedge deformable.

The self-locking fixing means in said wedge are advantageously formed by at least two separate blind lateral bores having an intersection and a longitudinal bore passing through the flange opposite the flange having a lateral bore and opening into said intersection, and said longitudinal bore and said lateral bores are advantageously adapted to receive said fixing band to form a loop.

Accordingly the free end of the fixing band is first passed though the first longitudinal bore into said intersection, exits the wedge through one of the two bores, is reinserted so that it enters said intersection again, and then exits in the opposite direction via said longitudinal bore, so that it rubs against the band portion that has already been inserted. This immobilizes the band relative to the wedge.

A preferred embodiment of the implant of the invention includes a single fixing band whose first end is connected to said wedge by said fixing means and whose second end is connected to said wedge by the self-locking fixing means formed in one of its lateral walls, and said wedge has, in the lateral wall opposite said lateral wall having the self-locking fixing means, guide means in which said fixing band can slide so that said band is able to surround said spinous processes and said wedge.

Accordingly the first end of the band is connected to the wedge at the level of the lateral bore and then surrounds the spinous process which is inserted into the first groove and rejoins the lateral wall having the guide means. The band then surrounds the spinous process which is inserted in the second groove and returns to the self-locking fixing means so that it is immobilized relative to the wedge.

It is particularly advantageous if the wedge is molded in one piece from a material obtained by polymerization. This means that wedges according to the invention can be produced at advantageous cost compared to wedges obtained by machining.

In one particular embodiment of the invention the wedge is made of polyether ether ketone.

In a second aspect, the invention provides a method of manufacturing an intervertebral implant, in particular of the above defined type, which method simplifies manufacture. This result is achieved due to the fact that the wedge of the implant is made by injection molding a polymer.

BRIEF DESCRIPTION OF THE DRAWINGS

Other features and advantages of the invention will emerge on reading the following description of particular embodiments of the invention, which are provided by way of non-limiting example; the description is given with reference to the accompanying drawings, in which.

DETAILED DESCRIPTION OF THE INVENTION

Figure 1:
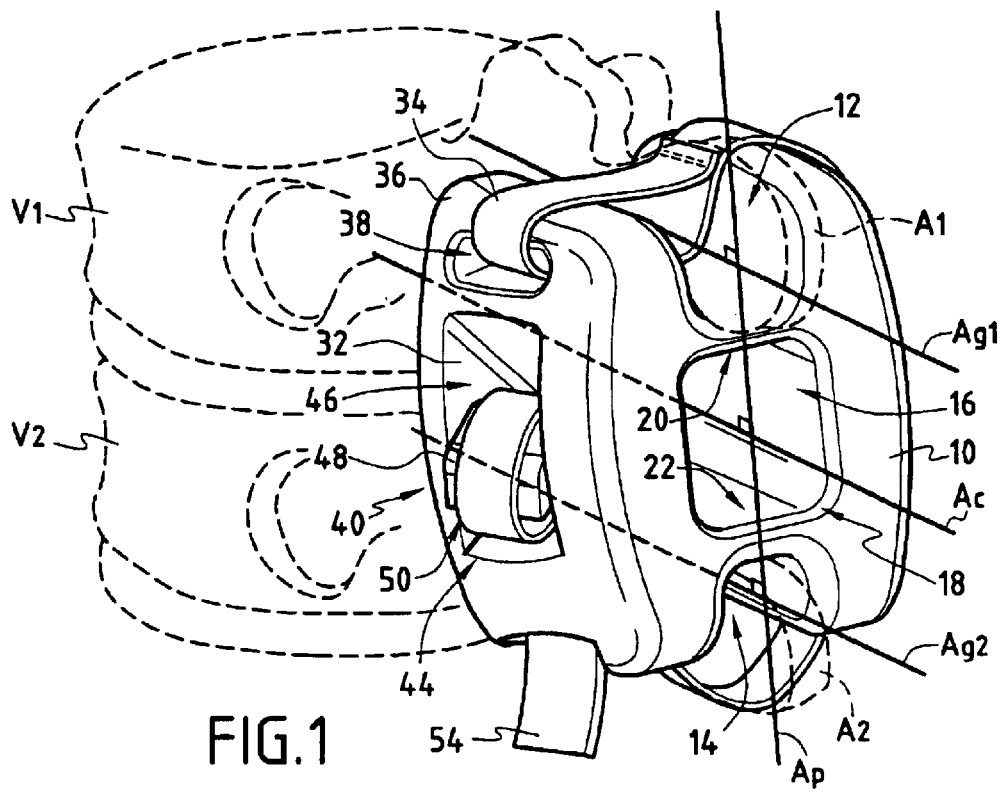
FIG. 1 is a diagrammatic perspective view of a first particular embodiment of a wedge inserted between the spinous processes of two consecutive vertebrae.

A first embodiment of the intervertebral implant according to the invention is described first with reference to FIG. 1.

FIG. 1 shows two consecutive vertebrae V1 and V2 extended in their posterior part by respective spinous processes A1 and A2. A wedge 10 having a top groove 12 and a bottom groove 14 is inserted between the spinous processes A1 and A2 so that to processes A1 engages in the groove 12 and the process A2 engages in the groove 14. The top groove 12 and bottom groove 14 have respective and substantially parallel axes Ag1 and Ag2.

The wedge 10 has a central opening 16 between the two grooves 12 and 14; the opening is of substantially rectangular parallelepiped shape and passes completely through said wedge 10. For practical reasons concerning the manufacture of said wedge 10, the corners 18 of the opening are rounded throughout the thickness of the wedge.

The central opening has an axis Ac substantially parallel to the axes Ag1 and Ag2 of the top groove 12 and the bottom groove 14.

The central opening 16 has a top face 20 parallel to a facing bottom face 22 and said faces 20, 22 are substantial perpendicular to an axis Ap intersecting the axes Ag1 and Ag2 of said grooves 12 and 14 and the axis Ac of the central opening at right angles.

Figure 2:
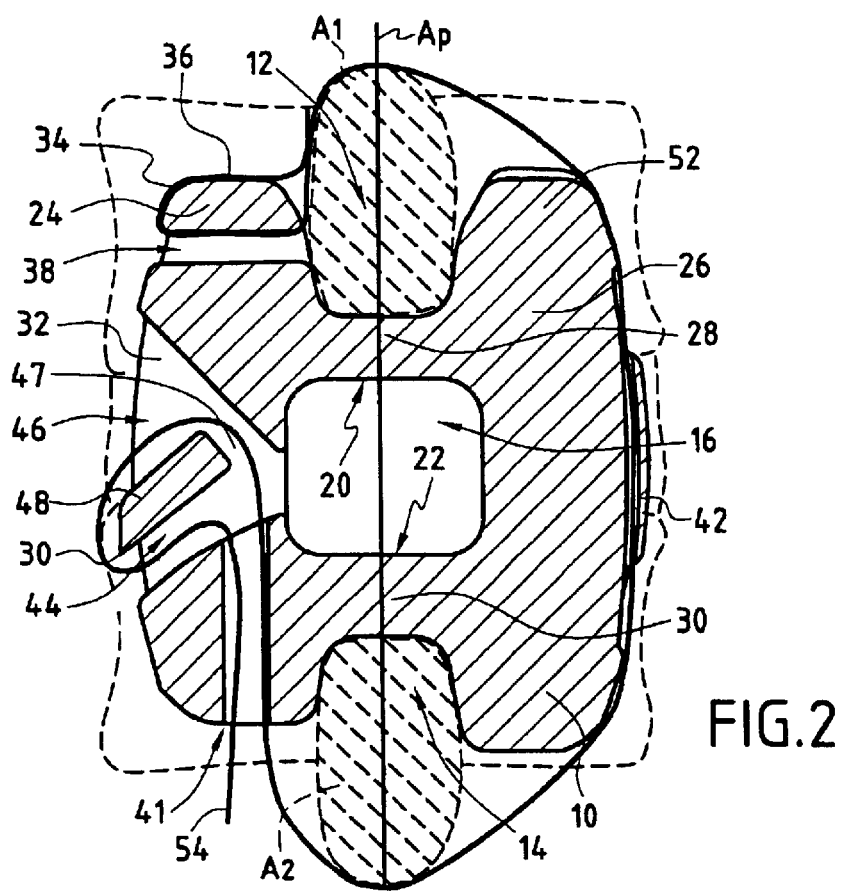
FIG. 2 is a diagrammatic view in vertical section of the wedge, shown in FIG. 1.

FIG. 2 to a rear view of the wedge 10, showing the axis Ap and the top face 20 and the bottom face 22 perpendicular thereto.

The wedge 10 is molded from a polymer material. However it could be machined from a block of polymer material. Wedges according to the invention are made from biocompatible materials.

The wedge 10 according to the invention is advantageously made of polyether ether ketone. This material has an intrinsically low coefficient of deformation under load and therefore a high modulus of elasticity, of the order of 3.5 GPs. However, the wedge 10 made from the above material deforms more readily because a central opening is formed in it.

The central opening 16 represents from 10 to 30% of the volume of the wedge. The width of the opening advantageously represents 38% of the total width of the wedge 10 and its height advantageously represents 40% of the total height of the wedge 10.

If the opening 16 represents 30% of the volume of the wedge 10, it deforms readily when a force is applied to it without its mechanical strength being compromised. On the other hand, if the opening 16 represents 10% of the volume of the wedge 10, it deforms relatively little, but with a greater amplitude then a wedge with no such opening.

It is therefore possible to adjust the capacity for deformation of the wedge 10 as a function of the specific applications for which it is intended by forming an opening of appropriate size.

As shown in FIG. 2, the central opening 16 divides the wedge 10 into two portions 24 and 26 joined by a top wall 28 and a bottoms wall 30. The top wall 28 and the bottom wall 30 respective constitute the bottom of the groove 12 and the bottom of the groove 14. Clearly the walls 28, 30 are thin relative to the portion of the wedge 10 between the two grooves 12 and 14 if the wedge 10 has no opening 16 and can be flexible relative to said portions 24 and 26.

Accordingly, as the spinous processes A1 and A2 move towards each other when the spine is extended, they tend aid to compress the two walls 28 and 30 and move them towards each other. Obviously, because of the opening and despite the high modulus of elasticity of the material, the two walls 28 and 30 are able to move elastically towards each other and therefore to allow a greater amplitude of movement of the two processes A1 and A2 relative to each other.

The compressive mechanical force exerted on the wedge causes deformation of the opening such that the two walls 28 and 30 move towards each other. However, the spine can also deform in other directions, as described in more detail in the remainder of the description.

In order to describe other deformations of the wedge 10, the method of fixing the wedge 10 to the spinous processes A1 and A2 in the manner shown is FIGS. 1 and 2 is described next.

This particular embodiment of the intervertebral implant according to the invention includes a single fixing band 32 for fastening the wedge 10 to the spinous processes A1 and A2.

The first end 34 of the band 32 is connected to the first flange 36 of the top groove 12 by means of a lateral bore 38 which is formed in the flange 36 and opens into the top groove 12. Accordingly, the first end 34 of the band 32 is inserted in the bore 38 to form a loop around the top portion of the flange 36 and is clipped to itself. This connects the band 32 firmly to the wedge 10 so that the band 32 can be tensioned without damaging the connection.

The band 32 surrounds the spinous processes A1 and A2 and the wedge 10 so that the processes are retained in the groove 12 and 14. To fix the band 32 and guide it on the wedge 10, the latter has self-locking fixing means 40 in one lateral wall and a longitudinal bore 41 and guide means 42 in the opposite lateral wall.

The self-locking fixing means 40 take the form of a first lateral bore 44 and a second lateral bore 46 which join at an intersection 47 within the thickness of the wedge. A longitudinal bore 41 passes through the flange of the groove and opens into the said intersection 47.

The wedge portion 48 between the two lateral bores 44 and 46 has a projecting transverse edge 50 adapted to constitute friction means for immobilizing the band 32.

Accordingly, the band 32, whose first end 34 is connected to the flange 36, bears on the top part of the spinous processes A1 and then on the and of the second flange 52 of the top groove 12, and is inserted in the guide means 42 on the lateral wall of the wedge 10. The band 32 then bears on the spinous process A2 and on the ends of the two flanges of the bottom groove 14. The free end 54 of the band 32 is inserted in the longitudinal bore 41 said crosses said intersection 47 to exit the wedge through the second bore 46; the band is then inserted in the first bore 44, crosses said intersection 47 again and exits through the longitudinal bore 41. Accordingly, the band 32 when tensioned is immobilized to translation by friction against itself in the longitudinal bore 41, The projecting edge 50 of the wedge portion 48 also immobilizes the band 32.

Thus the wedge 10 can be fastened to the spinous processes A1 and A2 by tensioning the band 32, which is immobilized relative to the wedge 10 in the self-locking means 40.

As a result, relative movement of the spinous processes A1 and A2 respectively trapped to the grooves 12 said 14 causes elastic deformation of the wedge 10, regardless of the direction of movement.

A second embodiment of an intervertebral implant in which the wedge has two openings is described next with reference to FIG. 3.

Figure 3:
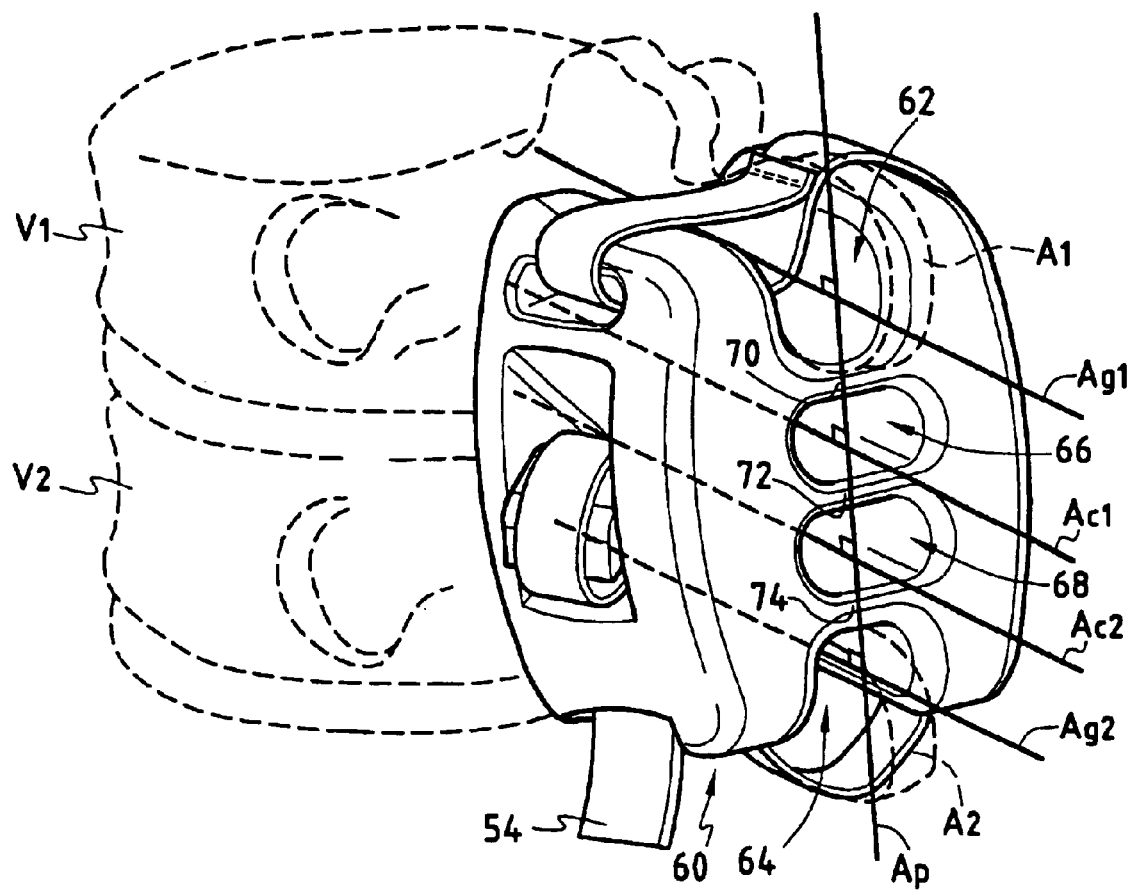
FIG. 3 is a diagrammatic perspective view of a second particular embodiment of a wedge inserted between the spinous processes of two consecutive vertebrae.

FIG. 3 shows a wedge 60 between two vertebrae V1 and V2 which are extended by respective spinous processes A1 and A2 which engage in a top groove 62 and a bottom groove 64 of the wedge 60. The wedge is connected to the spinous processes by a fixing band in a similar manner to the wedge 10 shown in FIGS. 1 and 2.

The wedge 60 has two superposed opening 66 and 68 with respective axes Ac1 and Ac2 substantially parallel to each other and to the axes Ag1 and Ag2 of said grooves 62 and 64. The superposed openings 66 and 68 have a shape including two parallel superposed faces and two facing curved walls.

Thus the wedge 60 is divided into two parts joined together by three partitions 70, 72 and 74 adapted to deform when a force is exerted on the wedge 60. Obviously, the capacities for deformation of the wedge 60 are less than that of the wedge 10 shown in FIGS. 1 and 2 because the two parts of the wedge 10 are connected by only two partitions. This is true only if the partitions 70, 72, 74 and 28, 30 are substantially the same size.

In this second particular embodiment of the invention, the self-locking means are also produced by forming two bores in the thickness of the lateral wall of the wedge 60 which meet at an intersection, and a longitudinal bore in the flange that opens into said intersection.

The previous two embodiments provide intervertebral implants including wedges with mechanical properties, in particular deformation properties, matching the reaction forces required to be exerted on the spinous processes when the latter move relative to each other.

The invention is not limited to the previous embodiments, but encompasses wedges having at least one opening in their central portion, regardless of the shape of said opening. In particular the opening can be circular.

What is claimed is:

1. An intervertebral implant including a wedge which is adapted to be inserted between two spinout processes, wherein said wedge has two opposite grooves each having an axis and each being defined by two flanges, the axes of said two grooves being substantially parallel to each other and for engagement of said spinous processes therein, said wedge has at least one central opening between said two grooves, said central opening passes completely through said wedge along an axis substantially parallel to the axes of said grooves, and the volume of said central opening is from 10% to 30% of the total volume of said wedge, which renders said wedge elastically deformable.

2. An intervertebral implant according to claim 1, wherein said wedge has two superposed openings between said two grooves, each opening having an axis, and the axes of said openings and the axes of said two grooves are substantially parallel to each other.

3. An intervertebral implant according to claim 2, including a single fixing band whose first end is connected to said wedge by said fixing means and whose second end is connected to said wedge by said self-locking fixing means formed in one of its lateral walls, and wherein said wedge further has, in the lateral wall opposite said lateral wall having the self-locking fixing means, guide means in which said fixing band can slide so that said band is able to surround said spinous processes and said wedge.

4. An intervertebral implant including a wedge which is adapted to be inserted between two spinous processes, wherein said wedge has two opposite grooves each having an axis and each being defined by two flanges, the axes of said two grooves being substantially parallel to each other and for engagement of said spinous processes therein, said wedge has at least one central opening between said two grooves, said central opening passes completely through said wedge along an axis substantially parallel to the axes of said grooves, and the volume of said central opening is from 10% to 30% of the total volume of said wedge, which renders said wedge elastically deformable; and wherein said wedge is made of polyether ether ketone.

5. An intervertebral implant according to claim 4, wherein said opening has a substantially rectangular parallelepiped shape with two parallel faces perpendicular to an axis intersecting the axes of said grooves at right angles.

6. An intervertebral implant according to claim 4, wherein said wedge has two superposed openings between said two grooves, each opening having an axis, and the axes of said openings and the axes of said two grooves are substantially parallel to each other, the intervertebral implant further including a single fixing band whose first end is connected to said wedge by said fixing means and whose second end is connected to said wedge by said self-locking fixing means formed in one of its lateral walls, and wherein said wedge further has, in the lateral wall opposite said lateral wall having the self-locking fixing means, guide means in which said fixing band can slide so that said band is able to surround said spinous processes and said wedge.

7. An intervertebral implant according to claim 4, including a fixing band adapted to retain said wedge between said processes, said wedge further having:
fixing means for connecting said band to said wedge, and
self-locking fixing means in its lateral walls adapted to receive said fixing band in order to immobilize it relative to said wedge,
wherein said fixing means include at least one lateral bore in one of said flanges opening into one of said grooves, and
wherein said self-locking fixing means include at least two separate blind lateral bores having an intersection and a longitudinal bore passing through the flange opposite the flange having a lateral bore and opening into said intersection, and said longitudinal bore and said lateral bores are adapted to receive said fixing band to form a loop.

8. An intervertebral implant including a wedge which is adapted to be inserted between two spinous processes, wherein said wedge has two opposite grooves each having an axis and each being defined by two flanges, the axes of said two grooves being substantially parallel to each other and for engagement of said spinous processes therein, said wedge has at least one central opening between said two grooves, said central opening passes completely through said wedge along an axis substantially parallel to the axes of said grooves, and the volume of said central opening is from 10% to 30% of the total volume of said wedge, which renders said wedge elastically deformable;

wherein said opening has a substantially rectangular parallelepiped shape with two parallel faces perpendicular to an axis intersecting the axes of said grooves at right angles.

9. An intervertebral implant according to claim 8, wherein said wedge has two superposed openings between said two grooves, each opening having an axis, and the axes of said openings and the axes of said two grooves are substantially parallel to each other, the intervertebral implant further including a single fixing band whose first end is connected to said wedge by said fixing means and whose second end is connected to said wedge by said self-locking fixing means formed in one of its lateral walls, and wherein said wedge further has, in the lateral wall opposite said lateral wall having the self-locking fixing means, guide means in which said fixing band can slide so that said band is able to surround said spinous processes and said wedge.

10. An intervertebral implant according to claim 8, including a fixing band adapted to retain said wedge between said processes, said wedge further having:
fixing means for connecting said band to said wedge, and
self-locking fixing means is its lateral walls adapted to receive said fixing band is order to immobilize it relative to said wedge,
wherein said fixing means include at least one lateral bore in one of said flanges opening into one of said grooves, and
wherein said self-locking fixing means include at least two separate blind lateral bores having an intersection and a longitudinal bore passing through the flange opposite the flange having a lateral bore and opening into said intersection, and said longitudinal bore and said lateral bores are adapted to receive said fixing band to form a loop.

11. An intervertebral implant including a wedge which is adapted to be inserted between two spinous processes, and a fixing band adapted to retain said wedge between said processes, wherein said wedge has two opposite grooves each having as axis and each being defined by two flanges, the axes of said two grooves being substantially parallel to each other and for engagement of said spinous processes therein, said wedge has at least one central opening between said two grooves, said central opening passes completely through said wedge along an axis substantially parallel to the axes of said grooves, and the volume of said central opening is from 10% to 30% of the total volume of said wedge, which renders said wedge elastically deformable;

said wedge further having:
fixing means for connecting said band to said wedge; and
self-locking fixing means in its lateral walls adapted to receive said fixing band in order to immobilize it relative to said wedge.

12. An intervertebral implant according to claim 4, wherein said fixing means include at least one lateral bore in one of said flanges opening into one of said grooves.

13. An intervertebral implant according to claim 11, wherein said opening has a substantially rectangular parallelepiped shape with two parallel faces perpendicular to an axis intersecting the axes of said grooves at right angles.

14. An intervertebral implant according to claim 11, wherein said wedge has two superposed openings between said two grooves, each opening having an axis, and the axes of said openings and the axes of said two groves are substantially parallel to each other, the intervertebral implant further including a single fixing band whose first end is connected to said wedge by said fixing means and whose second end is connected to said wedge by said self-locking fixing means formed in one of its lateral walls, and wherein said wedge further has, in the lateral wall opposite said lateral wall having the self-locking fixing means, guide means in which said fixing band can slide so that said band is able to surround said spinous processes and said wedge.

15. An intervertebral implant according to claim 8,
    wherein said fixing means include at least one lateral bore in one of said flanges opening into one of said grooves, and wherein said self-locking fixing means include at least two separate blind lateral bores having an intersection and a longitudinal bore passing through the flange opposite the flange having a lateral bore and opening into said intersection, and said longitudinal bore and said lateral bore are adapted to receive said fixing band to form a loop.

16. An intervertebral implant according to claim 8, wherein said wedge is made of polyether ether ketone.

* * * * *